United States Patent [19]

Ferres

[11] 4,215,120
[45] Jul. 29, 1980

[54] PENICILLIN ESTERS AND THEIR PREPARATION

[75] Inventor: Harry Ferres, Epsom, England

[73] Assignee: Beecham Group Limited, England

[21] Appl. No.: 922,978

[22] Filed: Jul. 10, 1978

[30] Foreign Application Priority Data

Jul. 14, 1977 [GB] United Kingdom ............... 29583/77

[51] Int. Cl.$^2$ ..................... A61K 31/50; A61K 31/43; C07D 499/44
[52] U.S. Cl. .................. 424/250; 260/239.1; 424/248.55; 424/267; 424/269; 424/271
[58] Field of Search ..................... 260/239.1; 424/271, 424/248.55, 250, 267, 269

[56] References Cited

U.S. PATENT DOCUMENTS

| 3,157,639 | 11/1964 | Doyle et al. .................. 260/239.1 |
| 4,081,546 | 3/1978 | Ferres .......................... 260/239.1 |

FOREIGN PATENT DOCUMENTS

| 675422 | 7/1952 | United Kingdom ................ 260/239.1 |
| 1470154 | 4/1977 | United Kingdom ................ 260/239.1 |

*Primary Examiner*—Norman Morgenstern
*Assistant Examiner*—Vera C. Clarke
*Attorney, Agent, or Firm*—Jacobs & Jacobs

[57] ABSTRACT

A class of esters of the penicillin, nafcillin have the general formula:

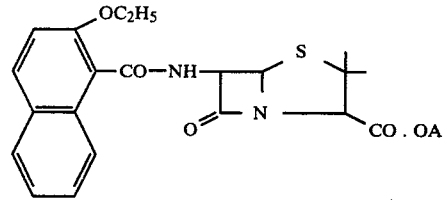

wherein A is a $C_1$-$C_6$ alkylene group substituted with one or two groups of formula —$NR^1 R^2$ and optionally further substituted with one or more methyl or ethyl groups, wherein $R^1$ and $R^2$ are the same or different and each is a $C_1$-$C_6$ alkyl group or $R^1$ and $R^2$ together with the nitrogen atom to which they are attached form a saturated 5- or 6- membered heterocyclic ring. Upon oral administration, the esters are absorbed into the bloodstream where they are hydrolyzed to release the antibacterially active parent penicillin, nafcillin.

9 Claims, No Drawings

PENICILLIN ESTERS AND THEIR PREPARATION

This invention relates to penicillins and in particular to a class of esters of the penicillin, nafcillin, which upon oral administration are absorbed into the bloodstream where they are hydrolyzed to release the antibacterially active parent penicillin.

The penicillin known as nafcillin has the structural formula (I):

(I)

According to the present invention, there is provided an ester of formula (II) or a pharmaceutically acceptable acid addition salt thereof:

(II)

wherein A is a $C_1$–$C_6$ alkylene group substituted with one or two groups of formula —$NR^1R^2$, and optionally further substituted with one or more methyl or ethyl groups wherein $R^1$ and $R^2$ are the same or different and each is a $C_1$–$C_6$ alkyl group or $R^1$ and $R^2$ together with the nitrogen atom to which they are attached form a saturated 5- or 6-membered hetereocyclic group.

Suitable acid addition salts of the compounds of formula (II) include, for example, inorganic salts such as the sulphate, nitrate, phosphate and borate; hydrohalides e.g., hydrochloride, hydroiodide; and organic acid addition salts such as acetate, oxalate, tartrate, maleate, citrate, succinate, benzoate, ascorbate, methanesulphonate and p-toluenesulphonate, trifluoroacetate.

A preferred acid addition salt is the hydrobromide.

Preferred groups A include $C_{1-3}$ alkylene, especially an ethylene group of formula —$CH_2$—$CH_2$—, substituted with one —$NR^1R^2$ group.

Suitable examples of alkyl groups for $R^1$ and $R^2$ include methyl, ethyl, n- and iso-propyl and n-, iso-, sec- and tert-butyl. Preferably $R^1$ and $R^2$ are the same and are both methyl or ethyl groups. When $R^1$ and $R^2$ complete a heterocyclic ring, they preferably comprise an alkylene chain optionally interrupted with an oxygen or nitrogen atom. Suitable rings include the following:

(wherein $R^3$ is hydrogen or alkyl).

Specific compounds falling within the scope of this invention include:

nafcillin dimethylaminoethyl ester, its hydroiodide, hydrobromide, and hydrochloride salts;

nafcillin diethylaminoethyl ester, its hydroiodide, hydrobromide, and hydrochloride salts;

nafcillin 4-methylpiperazine-1-ethyl ester, its hydroiodide, hydrobromide, and hydrochloride salts.

The esters of this invention may be prepared by esterification of nafcillin.

Thus the invention also provides a process for the preparation of compounds of formula (II) which process comprises reacting nafcillin of formula (I) above or a reactive esterifying derivative thereof with a compound of formula (III) or a reactive esterifying derivative thereof:

HO—A          (III)

wherein A is as defined with respect to formula (II).

By the term "reactive esterifying derivative" in relation to compounds (I) and (III) above, we mean derivatives of (I) and (III) which when reacted together take part in a condensation reaction with the consequent formation of an ester linkage:

—CO—O—A

Many methods of esterification using several different combinations of reactive esterifying derivatives are known from the literature. For example, the esterification reaction defined above may be achieved by reacting an activated ester of nafcillin with the alcohol (III). Preferred activated ester groups are mixed anhydrides, but other activated ester groups include the acid halide, e.g., acid chloride, and the reactive intermediate formed with a carbodiimide or carbonyldiimidazole.

Alternatively, nafcillin or a salt thereof, preferably the sodium or potassium salt, may be reacted with a halide, alkylsulphonyl (e.g. methansulphonyl) or arylsulphonyl (e.g. p-toluenesulphonyl) ester of compound (III).

The compounds of formula (II) may also be prepared by N-acylation of the corresponding esterified 6-aminopenam; that is by reacting a compound of formula (IV):

(IV)

or an N-protected derivative thereof, wherein A is as defined with respect to formula (II), with a reactive N-acylating derivative of the compound of formula (V):

$$\text{(V)} \quad \underset{\text{naphthalene with OC}_2\text{H}_5 \text{ and CO-OH}}{}$$

As the substituted amino ester grouping in formula (II) is labile to chemical hydrolysis, the above reaction should be carried out in anhydrous media.

Examples of "N-protected derivatives" of compound (IV) include N-silyl and N-phosphorylated derivatives.

By the term "N-silyl derivative" of compound (IV), we mean the product of reaction of the amino group of compound (IV) with a silylating agent such as a halosilane or a silazane of the formula:

$L_3$ Si U; $L_2$ Si $U_2$; $L_3$ Si $NL_2$;
$L_3$ Si NH Si $L_3$; $L_3$ Si . NH . COL; $L_3$ Si . NH . CO . NH . Si $L_3$;
L NH . CO . NH . Si $L_3$; LC . OSi $L_3$.
$\quad\quad\quad\quad\quad\quad\quad\quad\quad$ ||
$\quad\quad\quad\quad\quad\quad\quad\quad\quad$ NSiL$_3$ wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The term "N-phosphorylated" derivative of compound (IV) is intended to include compounds wherein the amino group of formula (IV) is substituted with a group of formula:

$-P.R_aR_b$ wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

A reactive derivative of compound (V) is employed in the above process.

Suitable derivatives of the acid (V) include an acid halide, preferably the acid chloride or bromide.

The acid halide may be prepared by reacting the acid (V) or a salt thereof with a halogenating (e.g. chlorinating or brominating) agent such phosphorus pentachloride, thionyl chloride or oxalyl chloride.

Alternatively, the N-acylating derivative of the acid (V) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid(V) are the acid azide, or activated esters such as esters with 2-mercapto-pyridine, cyanomethanol, p-nitrophenol, 2,4-dinitrophenol, thio-phenol, halophenol, including pentachlorophenolmonomethoxyphenol or 8-hydroxyquinoline; or amides such as N-acylsaccharins or N-acylnaphthalidmides; or an alkylidene iminoester prepared by reaction of the acid (V) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (V) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

A third method of preparation of the compounds of formula (II) comprises:

(a) reacting a compound of formula (VI):

$$\text{(VI)} \quad \underset{\text{β-lactam with R-NH, S, CH}_3, \text{CH}_3, \text{CO.O-A}}{}$$

wherein the group R is an organic acyl group (preferably of a naturally-occurring penicillin) and A is as defined with respect to formula (II), on the 6-amino atom;

(b) reacting the resulting compound to introduce a group $QR_f$ on the imino carbon atom, wherein Q is oxygen, sulphur or nitrogen and $R_f$ is an alkyl group of from 1 to 12 carbon atoms, or an aralkyl group of from 5 to 14 carbon atoms, to form an iminoether, iminothioether or amidine (when Q is O, S, or N respectively);

(c) reacting with a reactive derivative of an acid of formula (V) above and (d) treating with water or an alcohol.

The antibiotic compounds according to the invention may be formulated for administration in any convenient way for use in human or veterinary medicine, by analogy with other antibiotics, and the invention therefore includes within its scope a pharmaceutical composition comprising a compound of formula (II) above together with a pharmaceutical carrier or excipient.

The compositions may be formulated for administration by any route, such as oral topical or parenteral. The compositions may be in the form of tablets, capsules, powders, granules, lozenges, creams of liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone, fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous of oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg. of the active ingredient. The dosage as employed for adult human treatment will preferably range from 100 to 3000 mg. per day, for instance 1500 mg. per day, depending on the route and frequency of administration.

The ester of formula (II) may be the sole therapeutic agent in the compositions of the invention or a combination with other antibiotics may be employed. Advantageously the compositions also comprise a compound of formula (VII) or a pharmaceutically acceptable salt or ester thereof:

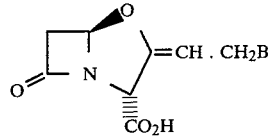

(VII)

wherein B is hydrogen or hydroxyl.

Preferably the compound of formula (VII) is clavulanic acid of formula (VIII) or a pharmaceutically acceptable salt or ester thereof:

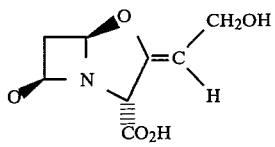

(VIII)

The preparation of these compounds is described in Belgium Patent Nos. 827,926, 836,652, and West German Offenlegungsschrift No. 2,616,088.

The following examples illustrate the preparation of some of the compounds of this invention.

SYNTHETIC DETAILS

General Procedure Used in All Cases for Synthesising the C-3 Alkylaminoalkyl Esters of 6-(2-ethoxy-1-naphthamido)penicillanic acid[nafcillin]

(a) Free Bases

Sodium 6-(2-ethoxy-1-naphthamido)penicillanate, monohydrate (1.13 g; 0.0025 M) was suspended in dry methylene dichloride (20 ml) at 0° C. and treated with pivaloyl chloride (0.3 ml; 0.002 M) and 2-3 drops of pyridine. After stirring at 0° C. for 1 hour the aminoalcohol (0.0023 M) was added in one portion. Stirring was continued for approximately 6 hours without external cooling. Any unreacted penicillin was removed by extracting the organic reaction mixture with water (3×25 ml).

(b) Hydroiodide Salts

The methylene dichloride reaction solution is shaken with glacial acetic acid (1 ml), water (10 ml) and sodium iodide (0.5 g) for 5 minutes. The aqueous layer is discarded and the organic layer dried over anhydrous magnesium sulphate. Methylene dichloride was removed in vacuo to yield an oil which is dissolved in the minimum quantity of ethyl acetate and left at 0° C. for crystallisation to occur. In the event that crystallisation could not be induced the ethyl acetate solution is concentrated in vacuo and added slowly, dropwise to petroleum ether, b.p. 40°-60° in order to precipitate the penicillin ester, hydroiodide as an amorphous solid.

(c) Hydrochloride Salt

As for hydroiodide salt except that sodium bromide is used.

(d) Hydrochloride Salt

The oily free penicillin ester free base is dissolved in ethyl acetate and one equivalent of hydrochloride in isopropanol added dropwise to the stirred ethyl acetate solution at 0° C. The hydrochloride salt is precipitated as an amorphous powder.

General formula IX:

![General formula IX structure showing naphthalene with OEt and CONH-penicillanate with COOR]

EXAMPLE 1

(a)

3-(2-N,N-Dimethylaminoethyl)-6-(2-ethoxy-1-naphthamido)penicillanate, hydroiodide (IX: R=—CH$_2$CH$_2$NMe$_2$.HI)

Product obtained as a white amorphous solid in 35% yield from 2-dimethylaminoethanol. $\nu_{max}$ (KBr) 3400 (broad), 1780, 1750, 1660, 1510, 1245 and 815 cm$^{-1}$, δ [(CD$_3$)$_2$SO] 1.38 (t) and 4.24 (q) (CH$_3$CH$_2$), 1.51 (s) and 1.62 (s) (gem methyls), 2.62 (s) (NMe$_2$), 3.16 (m) and 4.36 (m) (CH$_2$CH$_2$), 4.47 (s) (C$_3$ proton), 5.80 (m) (β-lactam, *NH+), 7.35–8.15 (m) (aromatic protons), 9.21 (m) (CONH*) *exchangeable with D$_2$O. Biochromatogram (B/E/W) Rf=0.90.

(b)

3-(2-N,N-Dimethylaminoethyl)-6-(2-ethoxy-1-naphthamido)penicillanate, hydrobromide (IX; R=—CH$_2$CH$_2$NMe$_2$.HBr)

Product obtained as a white amorphous solid in 20% yield from 2-dimethylaminoethanol. $\nu_{max}$ (KBr) 3400 (broad), 1780, 1750, 1660, 1510, 1245 and 1205 cm$^{-1}$. δ [(CD$_3$)$_2$SO] 1.37 (t) and 4.23 (q) (CH$_3$CH$_2$O), 1.50 (s) and 1.62 (s) (gem methyls), 2.73 (s) (N(CH$_3$)$_2$), 3.35 (m) and 4.48 (m) (CH$_2$CH$_2$) 4.52 (s) (C$_3$ proton), 5.82 (m) (β-lactams), 7.30–8.15 (m) (aromatic protons), 9.18 (d) (CONH*), +NH* gave a diffuse low-field resonance, *exchangeable with D$_2$O.

(c)

3-(2-N,N-dimethylaminoethyl)-6-(2-ethoxy-1-naphthamido)penicillanate, hydrochloride (IX; R=—CH$_2$CH$_2$NMe$_2$.HCl)

Product obtained as a white amorphous solid in 28% yield from 2-dimethylaminoethanol. (Found: C, 56.59, H, 6.27, N, 8.08, Cl$^-$, 6.91. C$_{25}$H$_{32}$ClN$_3$O$_5$S requires C, 57.52, H, 6.18, N, 8.05, Cl$^-$, 6.79. $\nu_{max}$ (KBr) 3400 (broad), 1780, 1750, 1660, 1520, 1245 and 1205 cm$^{-1}$. δ [(CD$_3$)$_2$SO] 1.37 (t) and 4.23 (q) (CH$_3$CH$_2$), 1.50 (s) and 1.61 (s) (gem methyls), 2.75 (s) (N(CH$_3$)$_2$), 3.40 (m) and 4.50 (m) (CH$_2$CH$_2$), 4.54 (s) (C$_3$ proton), 5.84 (m) (β-lactams), 7.30–8.15 (m) (aromatic protons) 9.15 (d) (CONH*), +NH* gave a diffuse low-field resonance, *exchangeable with D$_2$O.

EXAMPLE 2

3-(2-N,N-diethylaminoethyl)-6-(2-ethoxy-1-naphthamido)penicillanate, hydroiodide (IX; R=—CH$_2$CH$_2$NEt$_2$.HI)

Product obtained as a white crystalline solid in 39% yield from 2-diethylaminoethanol, m.p. 116°–119° C. (dec.) (Found: C, 51.2, H, 5.8 and N, 6.4%. C$_{27}$H$_{36}$IN$_3$O$_5$S requires C, 50.5, H, 5.5, N, 6.6%), $\nu_{max}$ (KBr) 1780, 1750, 1655, 1510 and 1245 cm$^{-1}$. δ [(CD$_3$)$_2$SO] 1.25 (t) and 3.42 (m) [N(CH$_2$CH$_3$)$_2$], 1.39 (t) and 4.25 (m) (OCH$_2$CH$_3$), 1.52 (s) and 1.62 (s) (gem dimethyls), 4.50 (s) (C$_3$ proton), 5.88 (m) (β-lactams), 7.35–8.20 (m) (aromatic H's), 9.21 (d) (CONH*) *exchangeable with D$_2$O biochromatogram (B/E/W) one zone Rf. 0.83.

EXAMPLE 3

3-(4-Methylpiperazine-1-ethyl)-6-(2-ethoxy-1-naphthamido)penicillanate, hydroiodide

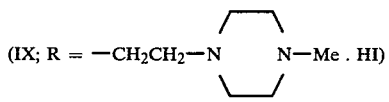

Product obtained as a white crystalline solid in 58% yield from 4-methylpiperazine-1 -ethanol. (Found: C, 50.5, H, 5.9, N, 8.0, S, 4.5 I$^-$, 19.2%. C$_{28}$H$_{36}$N$_4$O$_5$SI requires: C, 50.2, H, 5.6, N, 8.4, S, 4.8, I$^-$, 19.0%). $\nu_{max}$ (KBr) 3420 (broad), 1780, 1740, 1660, 1510, 1245 and 815 cm$^{-1}$. δ [(CD$_3$)$_2$SO] 1.32 (t) and 4.15 (q) (CH$_3$CH$_2$), 1.47 (s) and 1.58 (s) (gem methyls), 2.68 (m) 3.11 (m) and 4.19 (t) (ring CH$_2$'s and CH$_2$CH$_2$), 4.30 (s) (C$_3$ proton), 5.73 (m) (β-lactams), 7.2–8.02 (m) (aromatic protons), 9.10 (d) (CONH*), NH+* gave a diffuse low-field resonance, *exchangeable with D$_2$O., Biochromatogram (B/E/W) Rf.=0.9.

EXAMPLE 4

3-(1,3-Bisdimethylaminopropan-2-yl)-6-(2-ethoxy-1-naphthamido) penicillanate, dihydroiodide (AB 20138)

(IX; R=—CH(CH$_2$NMe$_2$)$_2$.2HI)

Product obtained as a white crystalline solid in 18% yield from 1,3-dimethylamino propan-2-ol. (Found: C, 42.2, H, 5.0, N, 6.8, S, 4.2, I$^-$ 32.1%. C$_{28}$H$_{42}$N$_4$O$_5$SI$_2$ requires: C, 42.1; H, 5.1, N, 7.0, S, 4.0, I$^-$ 31.8%). $\nu_{max}$ (KBr) 3410 (broad), 1780, 1755, 1660, 1510, 1245 and 815 cm$^{-1}$, δ [(CD$_3$)$_2$SO] 1.32 (t) and 4.15 (q) (CH$_3$CH$_2$), 1.53 (2s) (gem methyls), 2.85 (s) (2 NMe$_2$), 3.49 (m) (2 CH$_2$), 4.56 (s) (C$_3$ proton), 5.42 (m) (CH), 5.74 (m) (β-lactams), 7.16–8.02 (m) (aromatic protons) 9.11 (d) (CONH*), 2 NH+* gave diffuse low-field resonances, *exchangeable with D$_2$O.

HYDROLYSIS DATA

A comparison of the in vitro hydrolysis rates of the esters of Examples 1 to 4 (in the from of their hydroiodide salts) to nafcillin in human blood and in buffer control is shown in Table 1.

Table 1

In vitro hydrolysis data: Rates of conversion of nafcillin alkylamino alkyl esters to nafcillin in human blood and buffered saline (pH 7.4). (Substrate concentration equivalent to 100 μg/ml nafcillin free acid; Electrophoretic separation method).

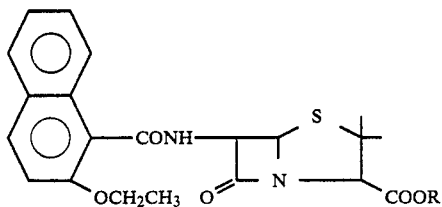

| Compound of Example No. | R | Hydrolysis System | 15 | 30 | 45 | 60 |
|---|---|---|---|---|---|---|
| 1(a) | —CH$_2$CH$_2$NMe$_2$ . HI | 90% Human Blood | 62 | 72 | 81 | 81 |
|  |  | Buffered Saline Control | 55 | 78 | 92 | 100 |
| 2 | —CH$_2$CH$_2$NEt$_2$ . HI | 90% Human Blood | 17 | 30 | 39 | 49 |
|  |  | Buffered Saline Control | 17 | 55 | 76 | 85 |
| 3 | —CH$_2$CH$_2$—N⟨ ⟩N—Me . HI | 90% Human Blood | trace | 13 | 27 | 29 |
|  |  | Buffered Saline Control | 19 | 53 | 55 | 56 |
| 4 | —CH(CH$_2$NMe$_2$)$_2$ . 2HI | 90% Human Blood | 68 | 80 | 87 | 105 |
|  |  | Buffered Saline Control | 94 | 98 | 105 | 107 |

Percentage hydrolysis to nafcillin at various times (in mins)

I claim:

1. An ester of formula (II) or a pharmaceutically acceptable acid addition salt thereof:

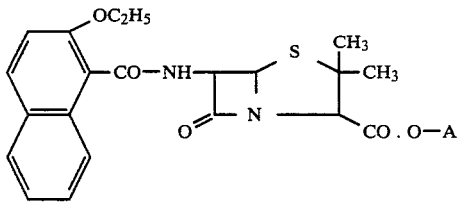

(II)

wherein A is a C$_1$-C$_6$ alkylene group substituted with one or two groups of formula —NR$^1$R$^2$ and optionally further substituted with one or more methyl or ethyl groups, wherein R$^1$ and R$^2$ are the same or different and each is a C$_1$-C$_6$ alkyl group or R$^1$ and R$^2$ together with the nitrogen atom to which they are attached form a saturated 5- or 6-membered heterocyclic ring.

2. An ester as claimed in claim 1 wherein A represents an ethylene group substituted with one —NR$^1$R$^2$ group.

3. An ester as claimed in claim 1 wherein R$^1$ and R$^2$ are the same and are methyl or ethyl groups.

4. 3-(2-N,N-Dimethylaminoethyl)-6-(2-ethoxy-1-naphthamido) penicillanate or an acid additon salt thereof.

5. 3-(2-N,N-Diethylaminoethyl)-6-(2-ethoxy-1-naphthamido) penicillanate or an acid addition salt thereof.

6. 3-(4-Methylpiperazine-1-ethyl)-6-(2-ethoxy-1-naphthamido) penicillanate or an acid addition salt thereof.

7. 3-(1,3-Bisdimethylaminopropan-2-yl)-6-(2-ethoxy-1-naphthamido) penicillanate or an acid addition salt thereof.

8. A compound as claimed in claim 1 wherein R$^1$ and R$^2$ in —NR$^1$R$^2$ together with the nitrogen atom to which they are attached form a saturated 5- or 6-membered heterocyclic ring.

9. An antibacterial pharmaceutical composition comprising a pharmaceutical carrier or excipient together with an antibacterially effective amount of a compound as claimed in claim 1.

* * * * *